United States Patent

Nishino et al.

Patent Number: 5,849,930
Date of Patent: Dec. 15, 1998

[54] PYRAZOLIDINE DERIVATIVE RADICAL SCAVENGER BRAIN-INFARCTION DEPRESSANT AND BRAIN-EDEMA DEPRESSANT

[75] Inventors: Chikao Nishino, Yokohama; Tatsuya Otake, Tokyo; Kentaro Adachi, Yokohama; Ryuhei Inada, Tokyo, all of Japan

[73] Assignee: Shiseido Co., Ltd., Tokyo, Japan

[21] Appl. No.: 741,032

[22] Filed: Oct. 30, 1996

Related U.S. Application Data

[63] Continuation of Ser. No. 617,707, Apr. 1, 1996, abandoned.

[30] Foreign Application Priority Data

Apr. 3, 1995 [JP] Japan ................. 7-101711

[51] Int. Cl.$^6$ ............ A61K 31/415; C07D 231/18; C07D 231/40
[52] U.S. Cl. .................. 548/370.4; 348/370.7; 348/371.4; 348/372.5; 514/403
[58] Field of Search ............. 548/370.4, 370.7, 548/371.4, 372.5; 514/403

[56] References Cited

U.S. PATENT DOCUMENTS

| 4,207,327 | 6/1980 | Lunsford et al. ............. 548/372.5 |
| 4,624,961 | 11/1986 | Welstead, Jr. . | |

FOREIGN PATENT DOCUMENTS

| A-0 208 874 | 1/1987 | European Pat. Off. . |
| A-0 449 195 | 10/1991 | European Pat. Off. . |
| 54-41873 | 4/1979 | Japan . |
| 2-207069 | 8/1990 | Japan . |

OTHER PUBLICATIONS

Kornet, Ali & Steinberg J. Heterocyclic Chem. 1993.
Uchiyama, Suzuki & Fukuzawa Jap.Jr. Pharmacology 1968.
Sod, Clinical Study of Free Radical, 1987.
Jap. Journal of Stroke, 1986.

Primary Examiner—Robert W. Ramsuer
Attorney, Agent, or Firm—Ronald R. Snider

[57] ABSTRACT

A pyrazolidine derivative or a salt thereof in accordance with the present invention is expressed by the following formula 1:

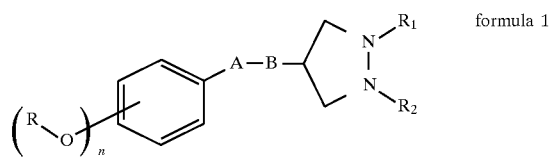

wherein A represents a group expressed by $-CH_2-$, $-CO-$, $-CS-$, $-CH_2CO-$, or $-CH=CH-CO-$; B represents a group expressed by $-O-$ or $-NH-$; n is an integer of 1 or 2; R represents an alkenyl group; and $R_1$ and $R_2$ represent a lower alkyl or benzyl group.

The pyrazolidine derivative above mentioned, as a radical scavenger, has antioxidant effect and lipid peroxidation inhibitory activity so as to be available for inhibiting brain infarction or brain edema.

17 Claims, 4 Drawing Sheets

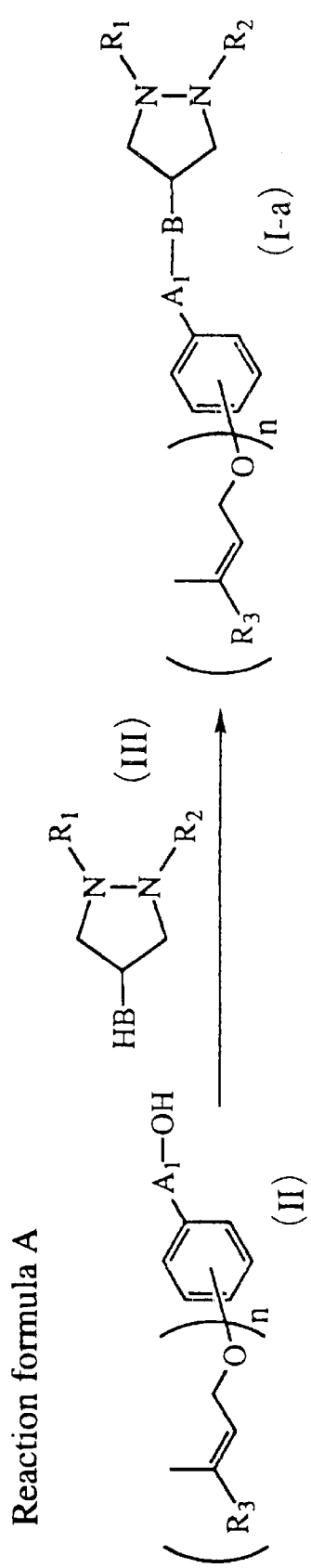
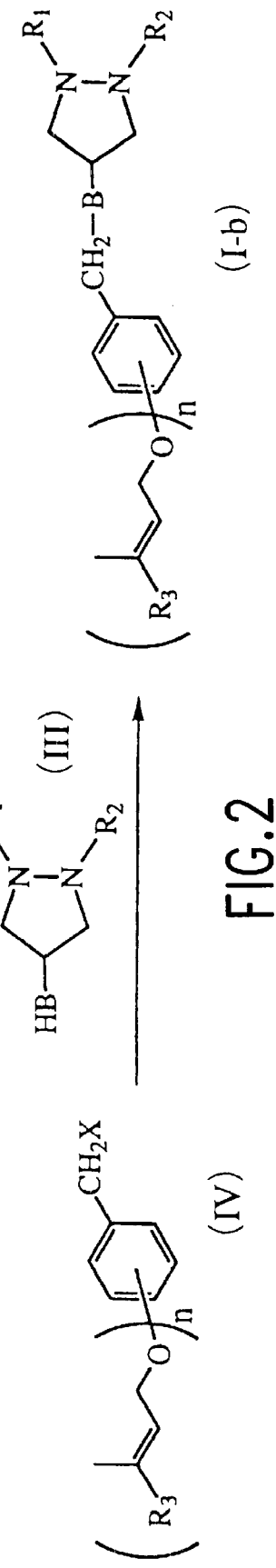

Reaction formula C
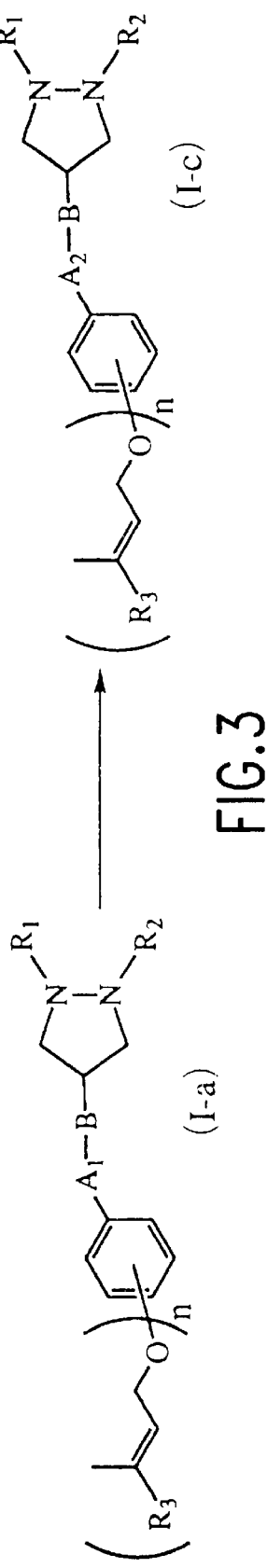
FIG.3
Reaction formula D
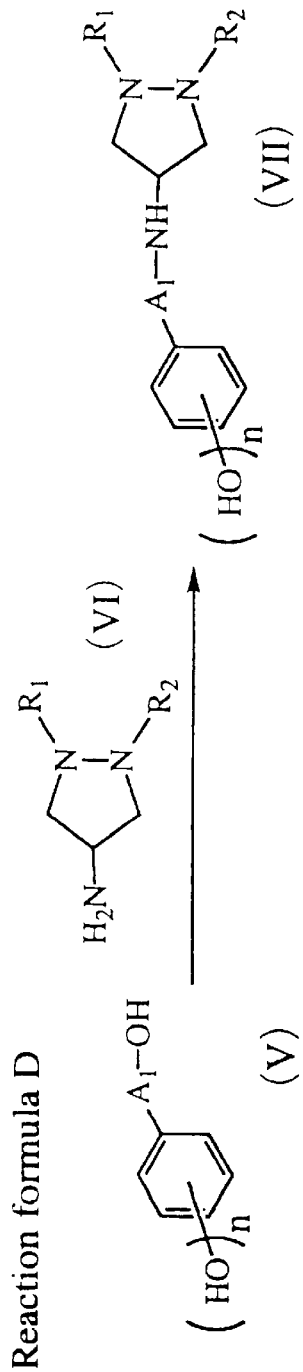
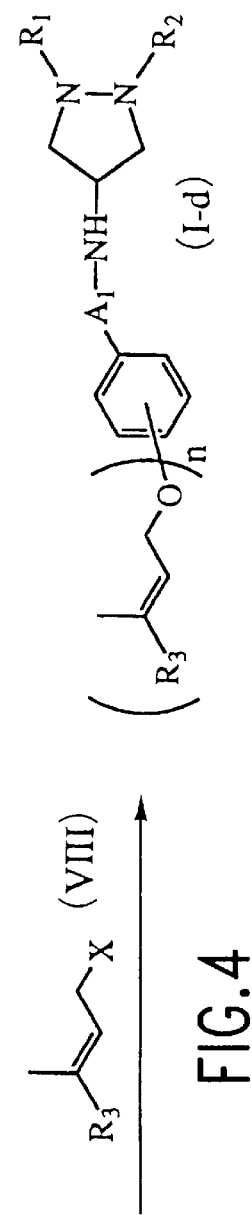
FIG.4

Reaction formula E

Reaction formula F

PYRAZOLIDINE DERIVATIVE RADICAL SCAVENGER BRAIN-INFARCTION DEPRESSANT AND BRAIN-EDEMA DEPRESSANT

RELATED APPLICATIONS

This application is a continuation of application Ser. No. 08/617,707, filed Apr. 1, 1996 now abandoned.

This application claims the priority of Japanese Patent Application No.7-101711 filed on Apr. 3, 1995, which is incorporated herein by reference.

FIELD OF THE INVENTION

The present invention relates to a pyrazolidine derivative and, in particular, to a derivative effective as a radical scavenger in organisms.

BACKGROUND OF THE INVENTION

In recent years, attention has been paid to influences of active oxygen and free radical upon organisms. Active oxygen and free radical are always generated and eliminated within an organism as long as the organism continues to live while using oxygen. In general, they act advantageously to the organism as a part of organism protection. However, when they are generated in an amount exceeding the protecting ability of the organism against the radical, they may attack the components of the organism constituting membranes and tissues of thereof, thereby causing various pathologies and malignancies. At present, the pathologies and diseases which may be attributable to active oxygen and free radical are numerous and their examples include cerebral nerves diseases such as brain infarction, brain edema, and parkinsonism; lung diseases such as lung oxygen intoxication and adult respiratory distress syndrome; circulation system diseases such as ischemic heart diseases (e.g., myocardial infarction and arrhythmia), and arteriosclerosis; and digestive organs diseases such as peptic ulcer, ulcerative colitis, and Crohn's disease.

Under these circumstances, consequently, there have been attempts to apply scavengers of active oxygen and free radical to medicaments for the above-mentioned diseases. For example, with respect to brain edema, mannitol, which is a mild radical scavenger, has been clinically used, though it is necessary continuous administration for two weeks. Recently, radical scavengers such as AVS (currently being applied) and MCI186 (currently being clinically tested in the third phase) have been developed recently. The sole target disease of these compounds is, however, brain edema. There has been no medical drug in which a radical scavenger is used for suppressing brain infarction.

On the other hand, a recombinant of SOD has become available and has been administered to patients so as to study its tissue-protecting effect. Acute myocardial infarction is one of its target diseases. By contrast, no radical scavenger other than SOD has been known as a medicament for this disease. With respect to arrhythmia, on the other hand only lidocain, which is a local anesthetic, has been clinically used.

SUMMARY OF THE INVENTION

In view of the foregoing prior art, an object of the present invention is to provide a low-molecular compound which is, as a radical scavenger, effective against brain edema and brain infarction.

Another object of the present invention is to provide a low-molecular compound which is effective against various diseases which are attributable to active oxygen and free radical.

As a result of diligent studies of the inventors for attaining the above mentioned objects, it has been found that a specific pyrazolidine derivative and its pharmacologically acceptable salts are effective, as a radical scavenger, against brain edema and brain infarction, thereby accomplishing the present invention.

Namely, a pyrazolidine derivative or a salt thereof in accordance with the present invention is expressed by the following formula 1:

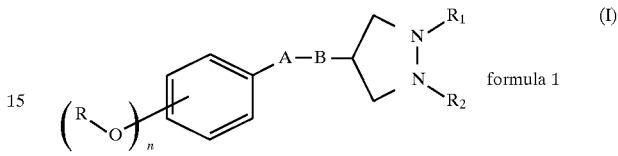

formula 1 wherein A represents a group expressed by —CH$_2$—, —CO—, —CS—, —CH$_2$CO—, or —CH=CH—CO—; B represents a group expressed by —O— or —NH—; n is an integer of 1 or 2; R represents an alkenyl group; and R$_1$ and R$_2$ represent a lower alkyl or benzyl group.

In formula 1, R is preferably a branched alkenyl group and, more preferably, a group expressed by R$_3$—C(CH$_8$)=CH—CH$_2$— in which R$_3$ represents methyl, prenyl, or geranyl group.

Also, in formula 1, each of R$_1$ and R$_2$ is preferably ethyl group. Further, in formula 1, A is —CO— group and B is —NH— group, preferably.

Also, a pyrazolidine derivative or a salt thereof in accordance with the present invention is preferably expressed by the following formula 2:

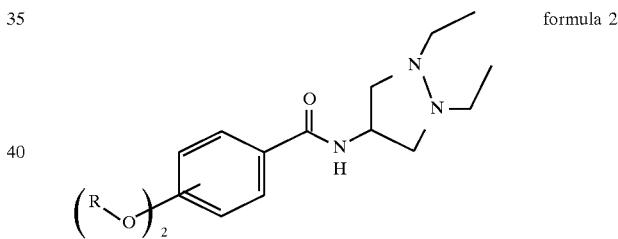

formula 2 wherein wherein R is a group expressed by R$_3$—C(CH$_3$)=CH—CH$_2$— in which R$_3$ represents an alkenyl group.

In formula 2, R$_3$ is preferably prenyl group.

Further, a pyrazolidine derivative or a salt thereof in accordance with the present invention is preferably expressed by the following formula 3:

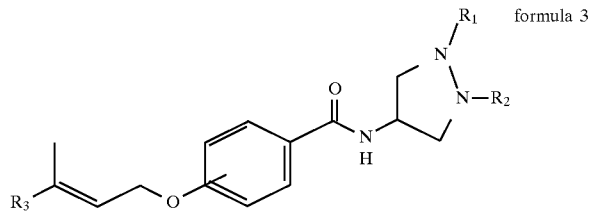

formula 3 wherein R$_3$ represents methyl, prenyl, or geranyl group and R$_1$ and R$_2$ represent a lower alkyl or benzyl group.

In formula 3, each of R$_1$ and R$_2$ is ethyl group and R$_3$ is prenyl group, preferably.

Furthermore, a pyrazolidine derivative or a salt thereof in accordance with the present invention is preferably expressed by the following formula 4:

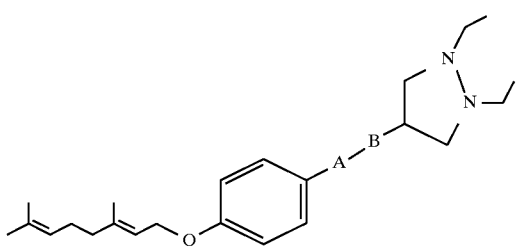

formula 4 wherein A represents a group expressed by —$CH_2$—, —CO—, —CS—, —$CH_2$CO—, or —CH=CH—CO— and B represents a group expressed by —O— or —NH—.

A radical scavenger in accordance with the present invention is characterized by comprising, as an effective ingredient, said pyrazolidine derivative or the pharmacologically acceptable salt thereof together with a pharmaceutically acceptable carrier and/or adjuvant.

A brain infarction depressant in accordance with the present invention is characterized by comprising, as an effective ingredient, said pyrazolidine derivative or the pharmacologically acceptable salt thereof together with a pharmaceutically acceptable carrier and/or adjuvant.

A brain edema depressant in accordance with the present invention is characterized by comprising, as an effective ingredient, said pyrazolidine derivative or the pharmacologically acceptable salt thereof, together with a pharmaceutically acceptable carrier and/or adjuvant.

A method for inhibiting a brain infarction in man or mammals in accordance with the present invention is characterized by administration to it of an effective amount of said pyrazolidine derivative or the pharmacologically acceptable salt thereof.

A method for inhibiting a brain edema in man or mammals in accordance with the present invention is characterized by administration to it of an effective amount of said pyrazolidine derivative or the pharmacologically acceptable salt thereof.

DETAILED DESCRIPTION OF THE INVENTION

In the following, the configuration of the present invention will be explained in further detail.

In the compound (I) in accordance with the present invention, alkenyl group found at R refers to a straight or branched alkenyl group which has at least one double bond and has 2 to 20 carbon atoms. It is preferably a branched alkenyl group and, more preferably prenyl, geranyl, neryl, or farnesyl group. While the double bond has two kinds of configurations, namely, cis and trans, each double bond in alkenyl group may have either configurations.

$R_1$ and $R_2$, which may be identical to or different from each otherare, lower alkyl or benzyl groups. Here, the lower alkyl group refers to a straight or branched alkyl group having 1 to 6 carbon atoms. Examples thereof include methyl, ethyl, n-propyl, n-butyl, isopropyl, isobutyl, 1-methylpropyl, tert-butyl, n-pentyl, 1- ethylpropyl, isoamyl, and n-hexyl groups. Preferably, they are ethyl groups.

Benzyl group found at $R_1$ and $R_2$ represents substituted or unsubstituted benzyl group. Here, its substituent is lower alkyl group, lower alkoxy group, lower alkoxy carbonyl group, carboxyl group, cyano group, nitro group, amino group which can be substituted by lower alkyl or lower acyl group, or halogen atom. Preferably, the substituent is a lower alkoxy group. Here, "lower alkyl group" is defined as mentioned above, "lower alkoxy group" refers to a group derived from the above mentioned lower alkyl group, "lower alkoxy carbonyl group" refers to a group derived from the above mentioned lower alkyl group, and "lower acyl group" refers to a straight or branched acyl group having 2 to 6 carbons, for example, acetyl, propionyl, butyryl, isobutyryl, and pivaloyl groups.

In formula 2 shown above, while alkenyl group found at $R_3$ includes that founded at R, it is preferably a branched alkenyl group and, more preferably, prenyl group. $R_3$ in formula 3 is methyl group, prenyl group, or geranyl group and, preferably, prenyl group.

The pyrazolidine derivative and its pharmacologically acceptable salts in accordance with the present invention, as a radical scavenger, have antioxidant effect and lipid peroxidation suppressing effect as well as a high safety. Accordingly, they are effective as medicaments for preventing and curing various damages attributable to radicals generated by ischemic reperfusion or the like such as brain infarction and brain edema. Also, they are expected to be effective against myocardial infarction and arrhythmia. Further, unlike the conventional radical scavengers, some kinds of the compound of the present invention have been found to be effective, by one drug, against both brain edema and brain infarction.

The compound of the present invention is a novel compound which has not been conventionally disclosed. As similar compounds, there have been known a pyrazolidine derivative having anti-vomiting effect in Japanese Unexamined Patent Publication No. 54-41873 (U.S. Pat. No. 4,207, 327), a pyrzolidine derivative having central nervous system effect, anti-vomiting effect, and gastrointestinal movement accelerating effect in Japanese Unexamined Patent Publication No. 2-207069, and a pyrazolidine derivative having memory improving effect in U.S. Pat. No. 4,624,961. However, as the compound which may relate to the pharmacological effect of the present invention, only the pyrazolidine derivative having anti-arrhythmia effect disclosed in J. Heterocyclic Chem. 30, 109 (1993), namely, 4-amino-N-(1,2-diethyl-4-pyrazolidinyl) benzamide, has been known. The pyrazolidinyl derivative in accordance with the present invention is characterized in that it has an alkenyloxy group or, preferably, substituted or unsubistituted prenyloxy group, on its basic skeleton of aromatic ring and thus is a novel compound which is different from the above mentioned known pyrazolidine derivatives.

The compound (I), which is expressed by formula 1, provided by the present invention can be made by reaction formulas A to E shown in FIGS. 1 to 5 in the following. As its manufacturing method, a general method disclosed in "New Experimental Chemistry Course" (Maruzen Co.) or "Peptide Synthesis" (Manizen Co.), for example, can be used.

First, in reaction formula A shown in FIG. 1, $A_1$ represents —CO—, —$CH_2$ CO—, or —CH=CH—CO—, while $R_1$, $R_2$, B, and n are defined as those in formula (I). $R_3$ is defined as that in formula 2 or formula 3.

In reaction formula A, when B is —NH—, from the carboxylic acid expressed by formula (II) and the amine expressed by formula (III), the amide compound in accordance with the present invention expressed by formula (I-a) is obtained. In this reaction, known amide-bond forming reactions such as a method proceeding by way of a mixed anhydride, a method proceeding by way of an acid chloride, a method using a condensing agent, a method using a carbonyl diimidazole, and a method proceeding by way of an azide can be used.

In the mixed anhydride method, an activator such as diphenylphosfinic chloride, phosphorus oxychloride, ethyl chloroformate, isobutyl cbloroformate, or pivaloyl chloride is used to convert the carboxylic acid (II) into its corresponding acid anhydride and then the latter is reacted with the amine compound (III). As an additive, for example, an organic base such as triethylamine, pyridine, or N-methylmorpholine is used. As a solvent, for example, a halogenated hydrocarbon such as dichloromethane or chloroform; an aromatic compound such as benzene, toluene, xylene, or pyridine; an ether such as tetrahydrofuran or dioxane; an anide such as N,N-dimethylformamide or N,N-dimethylacetamide; or dimethylsufloxide is used. While the reaction temperature and reaction time may be changed according to the material compounds used, the reaction is usually effected at a temperature within the range of –15° C. to the reflux temperature of the solvent.

In the acid chloride method, for example, phosphorus pentachloride, phosphorus trichloride, or thionyl chloride is used to convert the cart)oxylic acid (II) into its corresponding acid chloride and then the latter is reacted with the amine compound (III). As an additive, for example, an organic base such as triethylamine, pyridine, or N-methylmorpholine; an inorganic base such as sodium hydroxide; or a salt such as sodium acetate or potassium carbonate is used. As a solvent, for example, a halogenated hydrocarbon such as dichloromethane or chloroform; an aromatic compound such as benzene, toluene, xylene, or pyridine; an ether such as diethylether, tetrahydrofuran, or dioxane; an amide such as N,N-dimethylformamide or N,N-dimethylacetamide; dimethylsufloxide; water; or the mixture thereof is used. While the reaction temperature and reaction time may be changed according to the material compounds used, the reaction is usually effected at a temperature within the range of 0° C. to the reflux temperature of the solvent.

In the method using a condensing agent, for example, a carbodiimide such as N,N'-dicyclohexylcarbodiimide (DCC) or 1-ethyl-(3-dimethylaminopropyl) carbodiimide hydrochloride (WSCI) or a chloride such as titanium tetrachloride or silicon tetrachloride is used as the condensing agent. As a solvent, for example, a halogenated hydrocarbon such as dichloromethane or chloroform; an aromatic compound such as benzene, toluene, xylene, or pyridine; an ether such as tetrahydrofuran or dioxane; an amide such as N,N-dimethylformamide or N,N-dimethylacetamide; or dimethyl sufloxide is used. If necessary, this reaction may be effected while 1-hydroxy benzotriazole (HOBt) or N-hydroxysuccinimide (HONSu) is added thereto. While the reaction temperature and reaction time may be changed according to the material compounds used, the reaction is usually effected at a temperature within the range of 0° C. to the re-flux temperature of the solvent.

In the method using carbonyl diimidazole (CDI), 1,1'-carbonyldiimidazole is used to convert the carboxylic acid (II) into its corresponding N-acyl derivative and then the latter is reacted with the amine (III). As a solvent, for example, a halogenated hydrocarbon such as dichloromethane or chloroform; an aromatic compound such as benzene, toluene, or xylene, or an ether such as tetrahydrofuran or dioxane; an amide such as N,N-dimethylformamide or N,N-dimethylacetamide; or dimethyl sufloxide is used. While the reaction temperature and reaction time may be changed according to the material compounds used, the reaction is usually effected at a temperature within the range of 0° C. to the reflux temperature of the solvent.

In the azide method, an activator such as diphenylphosphorylazide is used to convert the carboxylic acid (II) into its corresponding azide and then the latter is reacted with the amine (III). As an additive, for example, an organic base such as triethylamine, pyridine, or N-methylmorpholine is used. As a solvent for example, a halogenated hydrocarbon such as dichloromethane or chloroform; an aromatic compound such as benzene, toluene, xylene, or pyridine; an ether such as tetrahydrofuran or dioxane; an amide such as N,N-dimethylformamide or N,N-dimethylacetamide; or dimethylsufloxide is used. While the reaction temperature and reaction time may be changed according to the material compounds used, the reaction is usually effected at a temperature within the range of 0° C. to the reflux temperature of the solvent.

Specifically, for example, in the method using the condensing agent, the carboxylic acid (II) is dissolved in dichloromethane, N,N-dimethylformamide, or the like and, after a condensing agent such as DCC or WSCI is added thereto, in or without the presence of HOBt or HOSu as an additive, and the resulting mixture is stirred, the amine (III) is added thereto and the reaction is effected at a temperature within the range of 0° C. to room temperature, thereby attaining the aimed object.

In reaction formula A, when B is —O—, from the carboxylic acid expressed by formula (II) and the alcohol expressed by formula (III), the ester compound expressed by formula (I-a) is obtained. Here, known ester-bond forming reactions such as a method using a dehydrating condensation and a method proceeding by way of an acid chloride can be used.

In the ester-bond formation by the dehydrating condensation, for example, methods using as a catalyst, a mineral acid such as sulfuric acid or hydrochloric acid, an organic acid such as p-toluene sulfonic acid, or a Lewis acid such as boron trifluoride etherate or methods using a coexisting desiccating agent such as magnesium sulfate anhydride or molecular sieve can be used. Also, a condensing agent such as trifluoroacetic anhydride or N,N'-dicyclohexylcarbodiimide (DCC) can be used. In this case, pyridine, 4-dimethylaminopyridine, or the like can be used therewith. Further, in the presence of triphenylphosphine, diethyl diazocarboxylate can be used. As a solvent, for example, a halogenated hydrocarbon such as dichloromethane or chloroform; an aromatic compound such as benzene, toluene, xylene, or pyridine; an ether such as tetrahydrofuran or dioxane; or an amide such as N,N-dimethylformamide or N,N-dimethylacetamide is used. While the reaction temperature and reaction time can be changed according to the material compounds used, the reaction is usually effected at a temperature within the range of 0° C. to the reflux temperature of the solvent.

In the acid chloride method, for example, phosphorus pentachloride, phosphorus trichloride, or thionyl chloride is used to convert the carboxylic acid (II) into its corresponding acid chloride and then the latter is reacted with the alcohol (III). As an additive, for example, an organic base such as triethylamine, pyridine, or N-methylmorpholine; an inorganic base such as sodium hydroxide; or a salt such as sodium acetate or potassium carbonate is used. As a solvent, for example, a halogenated hydrocarbon such as dichloromethane or chloroform; an aromatic compound such as benzene, toluene, xylene, or pyridine; an ether such as diethylether, tetrahydrofuran, or dioxane; an amide such as N,N-diiethylformamide or N,N-dimethylacetamide; dimethylsufloxide; water; or the mixture thereof is used. While the reaction temperature and reaction time may be changed according to the material compounds used, the reaction is usually effected at a temperature within the range of 0° C. to the reflux temperature of the solvent.

Specifically, for example, the carboxylic acid (II) is dissolved in dichloromethane, N,N-dimethylformamide, or the like and, after a condensing agent such as DCC or WSCI is added thereto in or without the presence of 4-dimethyl aminopyridine as an additive and the resulting mixture is stirred, the alcohol (III) is added thereto and the reaction is effected at a temperature within the range of 0° C. to room temperature, thereby attaining the aimed object.

In reaction formula B shown in FIG. 2, X represents a halogen atom while $R_1$, $R_2$, B, and n are defined as those of formula(I). $R_8$ is defined as that in formula 2 or formula 3.

In reaction formula B, when the halogen compound M and the compound (III) are reacted, the compound (I-b) of the present invention in which A in formula (I) is —$CH_2$— can be synthesized. This reaction can be effected in the presence of an base. Sodium amide, triethylamine, sodium hydride, sodium hydroxide, potassium carbonate, barium oxide, silver oxide, or the like is used therefor. Also, a catalytic amount of potassium iodide can be added thereto. As a solvent, for example, an alcohol such as methanol, ethanol, or butanol; an aromatic compound such as benzene, toluene, xylene, or pyridine; an ether such as diethylether, tetrahydrofuran, or dioxane; an amide such as N,N-dimethylformamide or N,N-dimethylacetamide; or a ketone such as dimethylsufloxide or acetone is used. While the reaction temperature and reaction time may be changed according to the material compounds used, the reaction is usually effected at a temperature within the range of 0° C. to the reflux temperature of the solvent.

Specifically, for example, the compound m is dissolved in tetrahydrofuran, N,N-dimethylformamide, or the like and, after sodium hydride or the like is added thereto and the resulting mixture is stirred, the halogen compound (IV) is added thereto. The reaction is effected at a temperature within the range of room temperature to the reflux temperature of the solvent, thereby attaining the aimed object.

In reaction formula C shown in FIG. 3, $A_1$ represents —CO—, —$CH_2$CO—, or —CH=CH—CO—, while $A_2$ represents —CS—, —$CH_2$CS—, or —CH=CH—CS—, $R_1$, $R_2$, B, and n are defined as those in formula (I). $R_8$ is defined as that in formula 2 or formula 3.

In reaction formula C, the compound expressed by formula (I-a) is converted into the compound expressed by formula (I-c), thereby yielding the compound of the present invention. Examples of the reagents used for this reaction include Lawesson's reagent (2,4-bis(4-methoxyphenyl)-1,3-dithia-2,4-diphosphetan-2,4-disulfide) and phosphorus pentasulfide. Also, when B is —NH—, imidoyl chloride formed by the reaction of the amide compound (I-a) with phosgene can be reacted with hydrogen sulfide to synthesize the thioamide compound (I-c). As a solvent, for example, a halogenated hydrocarbon such as dichloromethane or chloroform; an aromatic compound such as benzene, toluene, xylene, or pyridine; an ether such as tetrahydrofuran or dioxane; an amide such as N,N-dimethylformamide or N,N-dimethylacetamide; or dimethylsufloxide is used. While the reaction temperature and reaction time may be changed according to the material compounds used, the reaction is usually effected at a temperature within the range of 0° C. to the reflux temperature of the solvent.

Specifically, for example, the compound (I-a) is dissolved in toluene or the like, Lawesson's reagent is added thereto, and the reaction is effected at a temperature within the range of room temperature to the reflux temperature of the solvent, thereby attaining the aimed object.

In reaction formula D shown in FIG. 4, $A_1$ represents —CO—, —$CH_2$CO—, or —CH=CH—CO—, while X represents a halogen atom. $R_1$, $R_2$, and n are defined as those of formula (I) $R_3$ is defined as that in formula 2 or formula 3.

In reaction formula D, the carboxylic acid expressed by formula (V) and the amine compound expressed by formula (VI) are reacted to synthesize the amide compound (VII) and then, in the presence of an base, the latter is reacted with the alkenyl halide (VIII) so as to yield the compound of the present invention expressed by formula (I-d) is obtained. In this reaction, the amide-bond forming reaction at its first step can be effected under a reaction condition similar to that in reaction formula A. The subsequent reaction with the alkenyl halide (VIII) can be effected under a reaction condition similar to that in reaction formula B.

In reaction formula E shown in FIG. 5, $R_1$, $R_2$, and n are defined as those of formula (I). $R_3$ is defined as that in formula 2 or formula 3.

In reaction formula E, when the amide compound (I-e) is reduced, the amine derivative (I-f) in accordance with the present invention in which A is —$CH_2$— and B is —NH— in formula (I) can be obtained. As a reducing method, a general method can be used. Examples of the reducing agent used include aluminum hydride compounds such as lithium aluminum hydride; boron hydride compounds such as diborane, sodium borohydride, and sodium borohydride sulfide; silicon hydride compounds such as triethylsilane; and metal compounds such as Raney nickel. As an additive, cobalt chloride, zinc chloride, aluminum chloride, or the like can be used as well. As a solvent, for example, a halogenated hydrocarbon such as dichloromethane or chloroform; an aromatic compound such as benzene, toluene, xylene, or pyridine; an ether such as diethylether, tetrahydrofuran or dioxane; an alcohol such as methanol or ethanol is used While the reaction temperature and reaction time may be changed according to the material compounds used, the reaction is usually effected at a temperature within the range of 0° C., to the reflux temperature of the solvent.

Specifically, for example, lithium aluminum hydride is suspended in a solvent such as diethyl ether or tetrahydrofuran and, after the amide compound (I-e) is added thereto, the reaction is effected at a temperature within the range of 0° C. to the reflux temperature of the solvent, thereby attaining the aimed object.

On the other hand, the material compound (II) used in reaction formula A can be manufactured by reaction formula F shown in FIG. 6 as follows.

In reaction formula F, $A_1$ represents —CO—, —$CH_2$CO—, or —CH=CH—CO—, while $R_a$ represents a lower alkyl such as methyl, ethyl, isopropyl or tert-butyl group or benzyl group. X represents a halogen atom, while n is defined as those in formula (I). $R_3$ is defined as that in formula 2 or formula 3.

In reaction formula F, when the hydroxy compound (IX) is alkylated with the alkenyl halide (VIII) and then hydrolyzed, the carboxylic acid (II) can be synthesized. The first step of this reaction, namely, the alkylation reaction can be effected under a condition similar to that in reaction formula B. In the reaction of the second step, when the ester compound (X) is hydrolyzed in the presence of an acid or base, the carboxylic acid (II) can be synthesized. Hydrochloric acid, sulfuric acid, p-toluenesulfonic acid, or the like can be used as the acid, while sodium hydroxide, potassium hydroxide, potassium t-butoxide, or the like can be used as a base. As a solvent, a carboxylic acid such as formic acid or acetic acid, an alcohol such as methanol or ethanol, water, a mixed solvent thereof or the like can be used. While the reaction temperature and reaction time can be changed according to the material compounds used, the reaction is usually effected at a temperature within the range of 0° C. to the reflux temperature of the solvent.

Specifically, for example, the ester compound(X) is dissolved in an alcohol such as methanol or ethanol and, after an aqueous sodium hydroxide or potassium hydroxide solution is added thereto, the reaction is effected at a temperature within the range of room temperature to reflux temperature, thereby attaining the aimed object.

The material compound expressed by formula (IV) in reaction formula B can be synthesized by reaction formula G shown in FIG. 7 as follows.

In reaction formula G, $R_3$ represents a lower alkyl including methyl, ethyl, isopropyl, tert-butyl group, or the like or benzyl group, while X represents a halogen atom, $R_3$ is defined as that in formula 2 or formula 3, and n is defined as those in formula (I).

In reaction formula G, the ester compound (XI) can be reduced to synthesize the alcohol (XII) and then the latter can be halogenated to yield the halogen compound (IV). The first step of this reaction, namely, the reducing reaction can be effected under a condition similar to that in reaction formula E. The reaction of at the second step can be effected by a general halogenation reaction using a strong acid such as hydrochloric acid or hydrobromic acid, a phosphorus compound such as phosphorus tribromide, phosphorus trichoride, or phosphorus pentachloride, thionyl chloride, N-halogenosuccinimide and dimethylsulfide, or the like. Specifically, for example, the alcohol (XII) is added to a dichloromethane solution of N- chlorosuccinimide and dimethylsulfide and then the reaction is effected at a temperature within the range of 0° C. to room temperature, thereby attaining the aimed object.

Here, in the material compounds used in the above mentioned reaction formulas, those not specified, namely, compounds (III), (V), (VI), (VIII), and (IX) are commercially available or can be easily synthesized by known methods. For example, the amine (VI) can be synthesized by the method disclosed in Japanese Unexamined Patent Publication No. 57-59868, for example.

The compound expressed by formula (I) provided in accordance with the present invention can be changed to acid-added salts if necessary. Examples of the acid-added salts include salts in conjunction with inorganic acid such as hydrochloric acid, hydrobromic acid, sulfuric acid, or phosphoric acid and salts in conjunction with organic salts such as acetic acid, propionic acid, citric acid, lactic acid, oxalic acid, maleic acid, fumaric acid, succinic acid, tartaric acid, or methanesulfonic acid. These salts can be easily manufactured by normal methods.

When the pyrazolidine derivative in accordance with the present invention is used as a medicament for cerebral nerves diseases such as brain infarction and brain edema, it is generally used as a oral drug or an injection.

When the compound of the present invention is used as an oral drug, it may be administered orally as tablet, powder, granule, capsule, syrup, or the like as well as parenterally as suppository or the like. While the amount of administration may be outside of the range mentioned below according to the degree of symptom, personal difference, age, kind of symptom, or the like, it should of course be adjusted so as to fit the individual circumstances in specific cases. Usually 0.01 to 200 mg/kg or, preferably, 0.05 to 50 mg/kg or, more preferably, 0.1 to 10 mkg is administered per day for an adult in a single dose or several doses.

When formulating the medicament, a normal manufacturing method is used with a normal formulation carrier. If necessary, pharmacologically and pharmaceutically acceptable additives may be added thereto.

Namely, when preparing an oral solid formulation, after an excipient and, if necessary, a binder, a decaying agent, a luster, a coloring agent, a correctives, and the like are added to the main medicament, a normal method is used to form tablet, coated tablet, granule, powder, capsule, or the like.

Examples of the excipient include lactose, corn starch, sucrose, glucose, sorbitol, crystalline cellulose, and silicon dioxide, Examples of the binder include polyvinylalcohol, polyvinylether, ethyl cellulose, methyl cellulose, gum arabic, tragacanth, gelatin, shellac, hydroxypropyl cellulose, hydroxy propyl starch, and polyvinylpyrrolidone. Examples of the decaying agent include starch, agar, gelatin powder, crystalline cellulose, calcium carbonate, sodium hydrogencarbonate, calcium citrate, dextrin, and pectin. Examples of the luster include magnesium stearate, talc, polyethyleneglycol, silica, and hardened vegetable oil. As the coloring agent, those permitted to be added to medicines are used. Examples of the correctives include cocoa powder, menthol, aromatic acid, mentha oil, borneol, and cinnamon powder. If necessary, these tablet and granule can be coated with sugar-coating, gelatin-coating, and the like.

When the compound of the present invention is used as an injection, while the amount of administration may differ according to the degree of symptom, personal difference, age, or the like, usually 0.05 to 10 mg/kg or, preferably, 0.1 to 3 mg/kg is administered per day for an adult in a single dose or several doses.

The injection may be a sterile aqueous or non-aqueous solution, suspension, and emulsion. In such an injection, at least one active material is used as being mixed with at least one inactive aqueous diluent or inactive non-aqueous diluent. Further, if necessary, it may contain such adjuvants as antiseptic, wetting agent, emulsifier, dispersant, stabilizer, and dissolution adjuvant. In general, these are sterilized by filtration (e.g. by bacteria-blocking filter), compounding of sterilizer, or gamma-ray radiation or, after these treatments, turned into a solid composition by means of freeze-drying technique or the like and then sterile water or sterile injection diluent is added thereto immediately before use.

BRIEF DESCRIPTION OF THE DRAWINGS

FIGS. 1 to 5 shows examples of steps for manufacturing the pyrazolidine derivative in accordance with the present invention and FIGS. 6 and 7 shows examples of steps for manufacturing material compounds for synthesizing the pyrazolidine derivative in accordance with the present invention.

EXAMPLES

Figure 5:
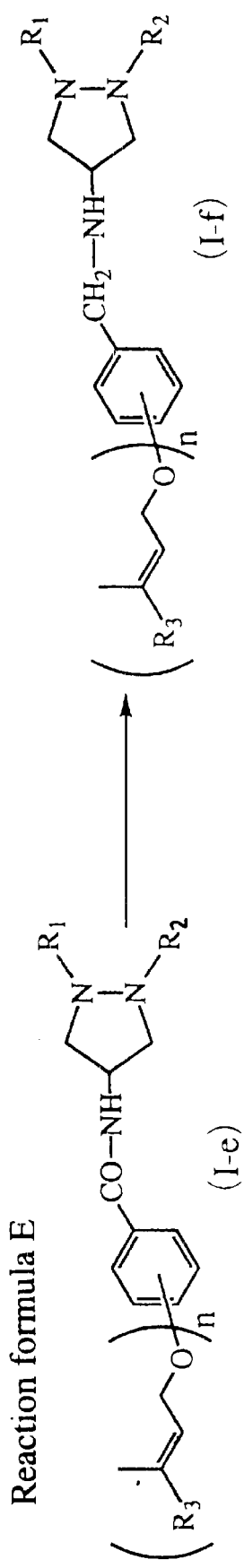
Figure 6:
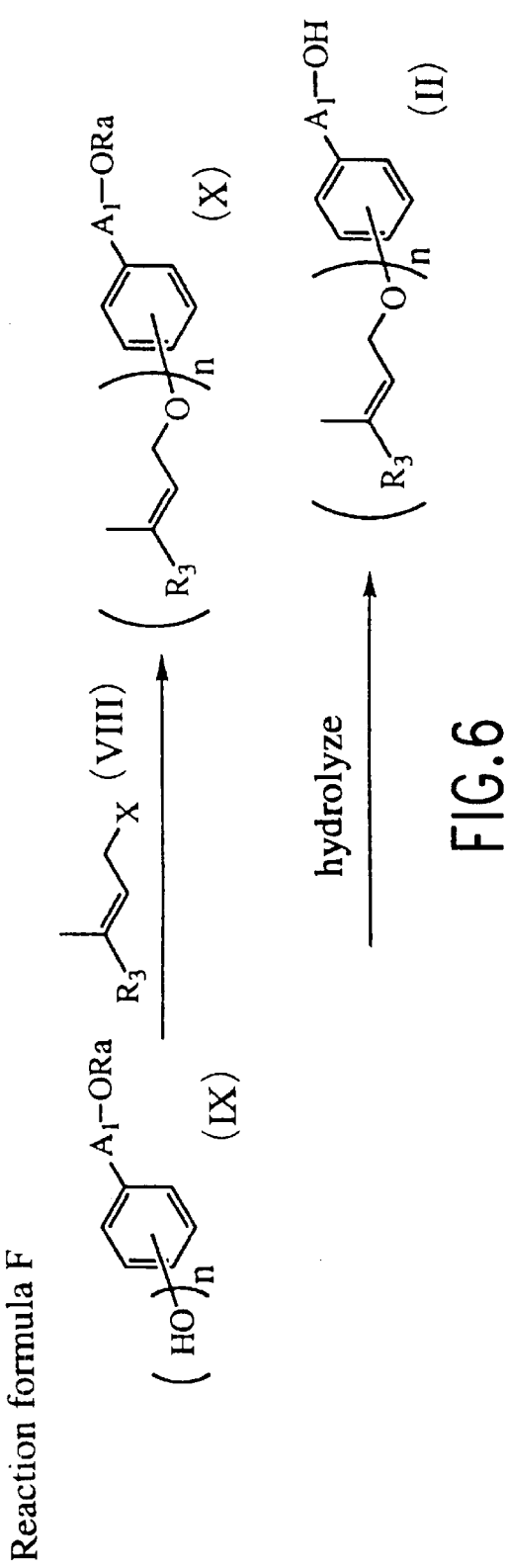
Figure 7:
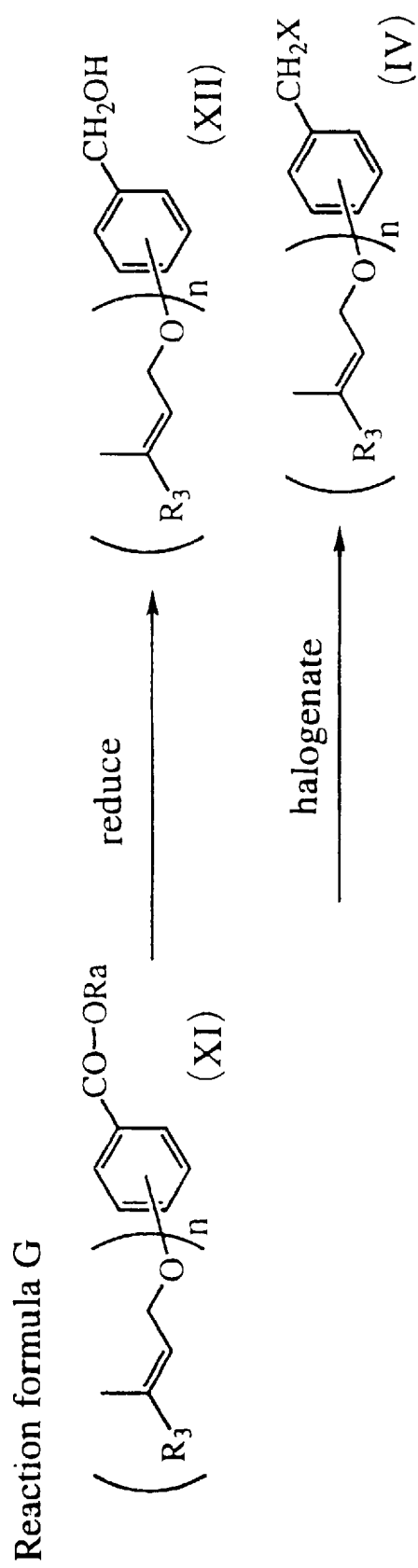

In the following, preferred examples of the present invention will be explained. However, the present invention should not be restricted to these examples.

Before the explanation of specific examples, the method for testing effects will be explained.

Radical Eliminating Effect Test(DPPH)

i) Meaning

Radical-eliminating ability of a sample drug is studied in terms of its reaction amount and reactivity with respect to $\alpha,\alpha$-diphenyl-$\beta$-picrylhydrazyl (DPPH) which is a stable radical.

ii) Method

Method of Uchiyama et al Japanese Journal of Pharmacology, vol. 88, pp. 678–683, 1968) was used. Namely, to a solution containing 20 mM acetic acid buffer (pH 5.5), 60% ethanol, and 10 $\mu$M of a sample compound, DPPH was added so as to yield a concentration of 0.1 mM. The resulting mixture was stirred and then its change in absorbance(ABS) at 517 nm was measured for 30 minutes at room temperature. Here, the sample compound was used as being dissolved in dimethyl sulfoxide (DMSO). While the final concentration of DMSO was 10%, no influence upon the present system was observed.

iii) Judgment Standard

The DPPH reducing ratio of the sample compound at the concentration of 10 $\mu$M was calculated by the following equation:

reducing ratio (%) [1-(ABS after 30 minutes/initial ABS)]×100

Lipid Peroxidation Inhibition Test i) Meaning

In an automatic oxidation system using a rat brain homogenate, whether a sample compound having a radical-eliminating effect can actually have a lipid peroxidation inhibitory activity or not is investigated and its effectiveness is comparatively studied.

ii) Method

With reference to method of Shimamoto et. al. (Clinical Study of Free Radical, vol. 1, pp. 91–95, 1987), the following method was used. An SD-line male rat (7-week-old) was bled to death with a physiological saline perfusion under pentobarbital anesthesia. Then, its hemisphaerium cerebri was taken out and, while being cooled with ice, a 19-fold amount of 20 mM phosphoric acid buffer (pH 7.4) was added thereto. The resulting mixture was homogenized. To this mixture, 1 $\mu$M of the sample compound was added. After the resulting mixture was incubated for 1 hour at 37° C., the amount of generated lipid peroxide was determined by TBA method Namely, to 0.2 ml of the homogenate, 0.2 ml of 8.1% SDS, 1.5 ml of 20% acetic acid buffer (pH 3.5), and 1.5 ml of 0.8% TBA reagent were added. The resulting mixture was incubated for 1 hour at 95° C. and then rapidly cooled with ice. Subsequently, 1 ml of distilled water and 5 ml of n-butanol/pyridine mixed solution (15:1, v/v) were added thereto and the mixture was stilled. After the mixture was centrifuged, the butanol layer was collected therefrom and its absorbance (a) at 535 nm was measured as compared with a blank. Also, as a reference liquid, a 10 $\mu$M solution of 1,1,3,3-tetraethoxypropane (TEP) was added in place of the brain homogenate and its absorbance (A) was measured in a similar manner. In the blank, a phosphoric acid buffer was used in place of the brain homogenate. The peroxide concentration was calculated by the following equation and defined as the brain lipid peroxide amount:

peroxide concentration (nmol MDA/g wet weight)=a/A× 100

The sample compound was used as being dissolved in dimethyl sulfoxide (DMSO). While the final concentration of DMSO was 2%, no influence upon the present system was observed iii) Judgment Standard The lipid peroxidation inhibitory rate of the sample compound at the concentration of 1 $\mu$M was calculated from the amount of increase in lipid peroxide in solvent-added group (M) and that in sample compound added group (m):

lipid peroxidation inhibitory rate(%)=(1-(m/M))×100

Brain Infarction Inhibition Test i) Meaning

The brain infarction inhibitory activity in vivo is studied. According to this test, it can be judged whether the peripherally administered sample compound can pass through the blood-brain barrier or not.

ii) Method

For the experiment, 9 to 10-week-old Crj:Fischer-344 line male rats were used. Each of all the soluble sample compounds was dissolved in a physiological saline and then administered intravenously or intraperitoneally. Each of insoluble ones was suspended in a physiological saline containing 0.1% Tween 80 and administered intraperitoneally. Also, those dissolved in a physiological saline containing 0.5% Tween 80 were used for intravenous administration. The intraperitoneal administration was effected 20 minutes before reperfusion, whereas the intravenous administration was effected simultaneously with reperfusion. As a control, only the base was administered The surgical operation was effected in a manner similar to method of Koizumi et, al. Japanese Journal of Stroke, vol, 8, pp. 1–8, 1986) so as to form a middle cerebral artery (MCA) infarction model. Namely, the rat was subjected to inhalation anesthesia with 4% halothane and then, while the anesthesia was maintained with 1% halothane, fixed on face-up position. The neck portion was subjected to median incision such that the common carotid artery and outer carotid artery around the right carotid artery branching portion were separated from their surrounding connecting tissues and then ligated with a silk string. Further, the inner carotid artery starting portion was surrounded by a silk string so as to be ready for ligation and fixation which would be effected after insertion of an embolus. Then, the common carotid artery was incised and, from there, an embolus having a length of about 16 min, in which a 4-0 surgical nylon string had been coated with a dental impression material, was inserted toward the inner carotid artery and its end near the nylon string was ligated and fixed to the inner carotid artery with the above mentioned silk string. Also, during the surgical operation, the body temperature was maintained by a small animal body temperature control apparatus in order to prevent it from lowering upon the whole anesthesia processes.

According to the foregoing operation, brain ischemia was effected for 2 hours and then the embolus was pulled out so as to effect reperfusion. The brain was taken out two hours after the reperfusion and then 4 pieces of crown-like separated strips were prepared by 2-mm intervals from the lambda level toward the downstream. These strips were immersed in 2% triphenyltetrazorium chloride (TTC) solution and incubated at 37° C. for 10 minutes. Thus dyed brain strips were immersed in a phosphate-buffered 8% formalin solution for 1 to 2 days and then photographed under a stereo-microscope (SZHIO ORINPAS). Thereafter, for each crown-like strip, the area of infarction region was measured by Planimeter (PILANX 5000 TAMAYA).

iii) Judgment Standard

The effects of the sample compound were represented by its individual inhibitory rate (%) which used the total area of the infarction regions which had not been dyed with TTC in the 4 strips.

The significance test was effected by student t-test.

individual inhibitory rate(%)=[I-(value in sample group/ value in control group)]×100

Brain Edema Inhibition Test i) Meaning

The brain edema inhibitory activity in vivo is confirmed. According to this test, it can be judged whether the peripherally administered sample compound can pass through the blood-brain barrier or not.

ii) Method

By using a 7 to 9 week- old Fischer rat (Charles River Japan Inc.), an MCA infarction reperfusion model was formed according to method of Koizumi et. al, (Japanese Journal of Stroke, vol. 8, pp. 1–8, 1986). Namely, the rat was fixed face-up position under anesthesia with 2% halothane and then its neck portion was subjected to median incision so as to separate the right common carotid artery therefrom to the carotid artery branching portion while carefully keeping the vagus nerve. The outer carotid artery and inner carotid artery around the carotid artery branching portion were separated front their surrounding connecting tissues and then ligated with a silk string. Further, the inner carotid artery starting portion was surrounded by a silk string so as to be ready for ligation and fixation which would be effected after insertion of an embolus string. Then, the common carotid artery was incised and, from there, an embolus string was inserted toward the inner carotid artery by about 15 to 16 mm and then ligated and fixed to the inner carotid artery with the above mentioned silk string. As a result of the foregoing operation, the tip of the embolus string proceeded beyond the MCA branching portion so as to enter the anterior cerebral artery by about 1 to 2 mm and formed infarction at the MCA inlet by the body portion of the embolus string. After the embolus string blocking the MCA starting portion was left for a predetermined time, it was pulled out under halothane anesthesia to effect reperfusion. Here, in this model, since the right common carotid artery has been ligated, the blood flow is supposed to be restarted from the left inner carotid artery and vertebrobasilar arteries by way of the anterior and posterior communicating arteries. This experiment effected two-hour ischemia and two-hour reperfusion.

Here, the embolus string was prepared in the following manner. Namely, a tip of a 4-0 surgical nylon string having a total length of 16 mm was held over an alcohol lamp so as to form a ball with a diameter of 0.2 to 0.3 mm and then a length of about 5 mm on the nearer side therefrom was coated with a dental impression material with reference to the size of the ball, thereby forming the embolus string.

The brain moisture content was measured by wet and dry weight method. Namely, after the head of the animal which had been subjected to ischemia or ischemic reperfusion was severed and its brain was taken out. After the resection of the cerebellum, the fore-brain was separated into right and left hemispheres which were immediately weighed respectively as ischemia side and non-ischemia side, thereby yielding their wet weight. Further, after being dried at 110° C. for 24 hours, their weight was measured again to yield dry weight. From thus obtained wet weight and dry weight, the brain moisture content was determined by the following equation:

brain moisture content (%)=((wet weight–dry weight)/wet weight)×100

The sample compound was suspended in a 0.05% Tween 80/physiological saline and, with an administration concentration of 100 mg/kg, 5 ml/kg was intraperitoneally administered 20 minutes before reperfusion. Also, to a control, the base was administered alone in a similar manner.

iii) Judgment Standard

The results obtained were expressed by mean value±standard deviation.

The significance test was effected by unpaired t-test or Welch's t-test and the difference was considered to be significant when the level of significance was less than 5% (P<0.05). The inhibitory rate was expressed by the following equation:

inhibitory rate(%)=((brain moisture content in control group–brain moisture content in sample group)/(brain moisture content in control group–brain moisture content in two-hour ischemia group))×100

Compound Group 1

This group corresponds to the above mentioned formula 2 wherein n is 2, A is —CO—, B is —NH—, $R_1$ and $R_2$ are ethyl group, and $R_3$ is prenyl group.

Example 1:

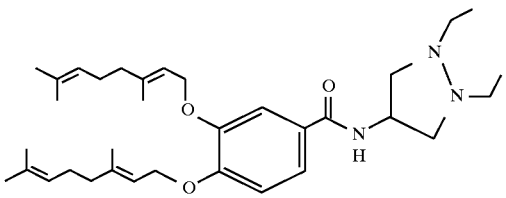

Example 2:

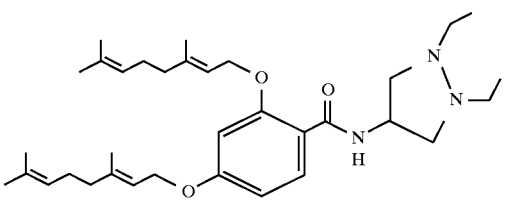

Example 3:

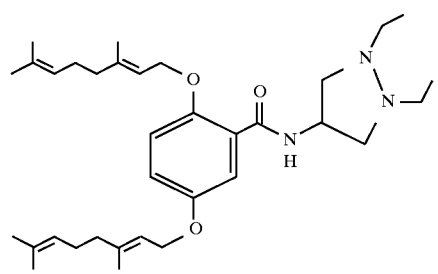

Example 4:

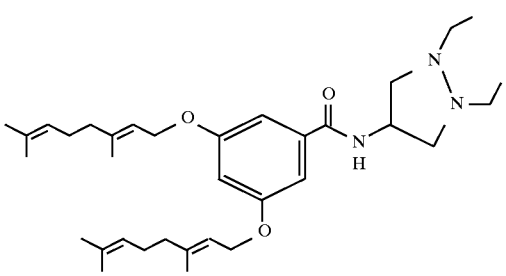

TABLE 1

| Sample compound | DPPH | Lipid peroxidation Inhibition | Brain Infarction Inhibition |
|---|---|---|---|
| Example 1 | 36.5 | 27.8 | |
| Example 2 | 61.0 | 24.7 | |
| Example 3 | 53.4 | 23.6 | |
| Example 4 | 41.3 | 33.5 | 7.4(100 mg/kg, ip) |

As can be seen from the foregoing examples, the materials belonging to this group has a high DPPH reducing effect (radical-eliminating effect) as well as a lipid peroxidation inhibitory activity. This tendency is widely recognized independent of the bonding position of —O—R group.

Compound Group 2

This group corresponds to the above mentioned formula 3 wherein n is 1, A is —CO—, and B is —NH—.

Example 5:

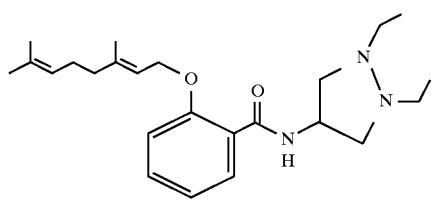

Example 6:

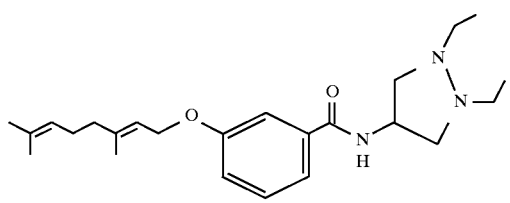

Example 7:

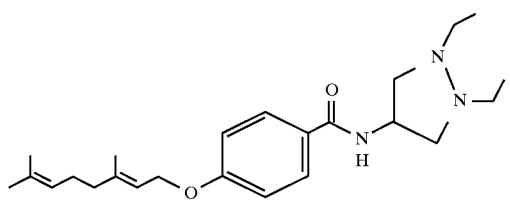

Example 8:

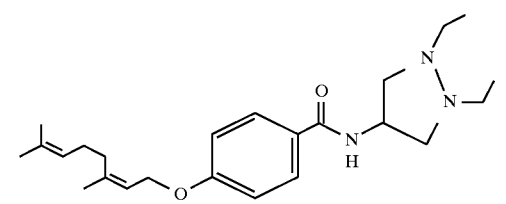

Example 9:

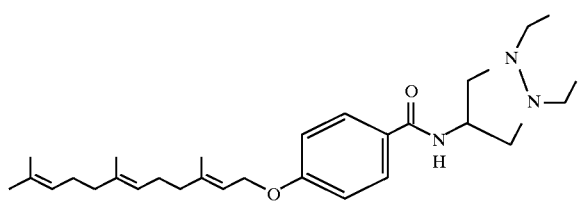

Example 10:

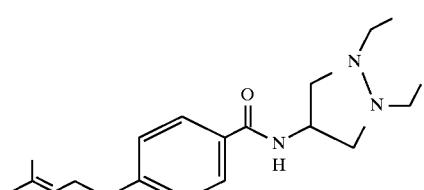

Example 11:

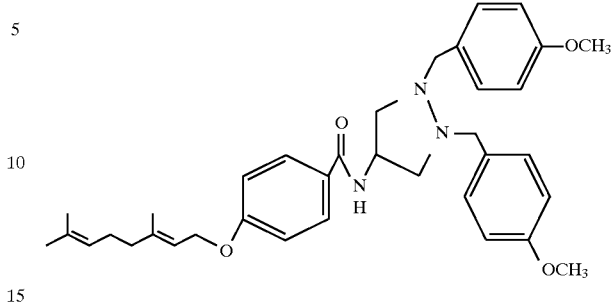

TABLE 2

| Sample compound | DPPH | Lipid peroxidation Inhibition | Brain Infarction Inhibition | Brain Edema Inhibition |
|---|---|---|---|---|
| Example 5 | 45.5 | 21.5 | | |
| Example 6 | 29.9 | 29.1 | | |
| Example 7 | 28.4 | 14.9 | 89.1(30 mg/kg,ip) 48.0(3 mg/kg,iv) | 11.7 (100 mg/kg,ip) |
| Example 8 | 31.9 | 25.1 | | |
| Example 9 | 33.0 | 32.0 | | |
| Example 10 | 30.5 | 21.2 | | 8.6 (100mg/kg,ip) |
| Example 11 | 14.4 | 13.0 | | |

As can be seen from the foregoing examples, the materials belonging to this group has a high DPPH reducing effect (radical-eliminating effect) as well as a lipid peroxidation inhibitory activity. Also, the compound of Example 7, for example, exhibits an excellent effect of inhibition both brain infarction and brain edema. Such a compound, which is effective against both brain edema and brain infarction alone, is quite rare.

In this group, $R_3$ can be configured with a high degree of freedom, whereby various alkyl and alkenyl groups can be used.

Compound Group 3

This group corresponds to the above mentioned formula 4 wherein $R_1$ and R are ethyl group, n is 1, and —O—R group is bonded to para-position.

Example 12:

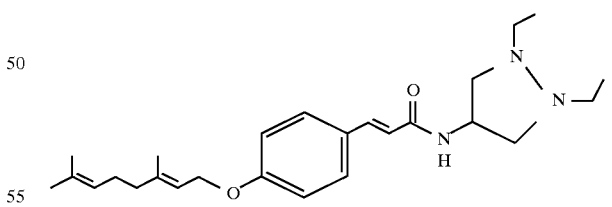

Example 13:

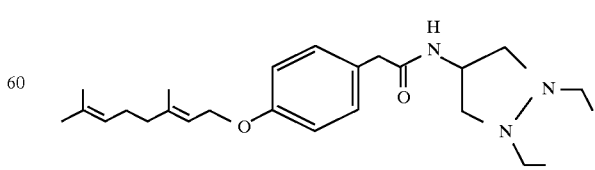

Example 14:

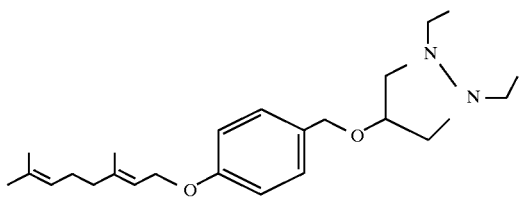

Example 15:

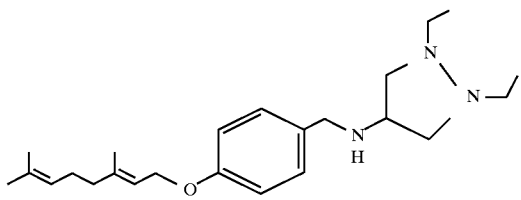

Example 16:

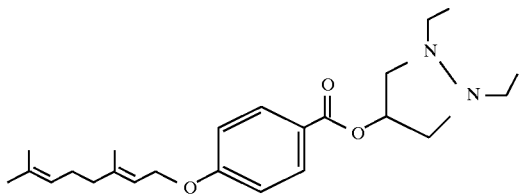

Example 17:

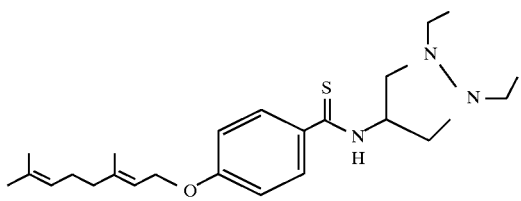

TABLE 3

| Sample compound | DPPH | Lipid peroxidation Inhibition |
| --- | --- | --- |
| Example 12 | 25.1 | 23.6 |
| Example 13 | 32.3 | 21.8 |
| Example 14 | 56.3 | 13.7 |
| Example 15 | 39.5 | 15.3 |
| Example 16 | 22.2 | 16.8 |
| Example 17 | 24.2 | 39.8 |

As can be seen from the foregoing examples, the materials belong to this group has a high DPPH reducing effect (radical-eliminating effect) as well as a lipid peroxidation inhibitory activity.

In this group, A and B can be selected with a high degree of freedom, whereby A may be —CH$_2$—, —CO—, —CS—, —CH$_2$CO—, or —CH═CH—CO—, while B may be —O— or —NH—.

In the following, synthetic methods of the typical material compounds used for synthesizing the compound of the present invention will be shown as reference examples.

Reference Example 1
Synthesis of 4-geranyloxybenzoic acid

To a solution of methyl 4-hydroxybenzoate (7.61 g) in acetone (80 ml) were added geranyl bromide (10.9 g) and potassium carbonate (13.8 g). The mixture was refluxed with heating for 6 hours. The reaction solution, after water (150 ml) were added thereto, was extracted with chloroform. The extract was dried over sodium sulfite anhydride and then concentrated under a vacuum. The residue was purified by silica gel column chromatography (n-hexane:ethyl acetate= 9:1), thereby yielding 13.00 g (90%) of methyl 4-geranyloxybenzoate.

To a solution of methyl geranyloxybenzoate (13.00 g) in methanol (50 ml) was added an aqueous solution (10 ml) of potassium hydroxide (3.90 g), After being stirred at room temperature for one night, the mixture was refluxed with heating for 1 hour. Concentrated hydrochloric acid was added to the reaction solution so as to acidified. Then, the resulting solution was extracted with chloroform. The extract was dried over sodium sulfate anhydride and then the solvent was evaporated under a vacuum. The residue was recrystallized from an n-hexane/ethyl acetate mixed solution, thereby yielding 9.77 g (71%) of the aimed compound.

Reference Example 2
Synthesis of 4--geranyloxybenzylalcohol.

To a solution of methyl 4- hydroxybenzoate (33.2 g) in acetone (300 ml) were added geranyl bromide (44.5 g) and potassium carbonate (55.2 g). The mixture was refluxed with heating for 2 hours. The reaction solution, after water (200 ml) were added thereto, was extracted with chloroform (400 ml). The extract was dried over sodium sulfate anhydride and then concentrated under a vacuum to yield a raw product of methyl 4-geranyloxybenzoate.

To a suspension of lithium aluminum hydridete (7.59 g) in trahydrofuran (200 ml) was added a solution of the raw product of methyl 4-geranyloxybenzoate in tetrahydrofuran anhydride (100 ml) dropwise while being cooled with ice. After being stirred for 1 hour at room temperature, the reaction solution, with water (200 ml) added thereto, was extracted with ethyl acetate (400 ml). The extract was dried over sodium sulfite anhydride and then the solvent was evaporated under a vacuum. The residue was recrystallized from an n-hexane/ethyl acetate mixed solution, thereby yielding 34.4 g (66%) of the aimed compound.

Reference Example 3
Synthesis of 1,2-diethyl-4-hydroxypyrazolidine

To an aqueous solution (100 ml) of potassium carbonate (8.58 g) were added diethylhydrazine dihydrochloride (10.0 g) and chloromethyloxylan (6.32 g). After being stirred with heating at 60° C. for 4 hours, the reaction solution was extracted with chloroform, dried oversodium sulfite anhydride, and then concentrated under a vacuum The residue was purified by silica gel column chromatography (chloroform:methanol =20:1), thereby yielding 3.45 g (39%) of the aimed compound.

Reference Example 4
Synthesis of 4- amino-1,2-bis(4- methoxyphenylmethyl) pyrazolidine To a solution of 4- methoxybenzaldehyde (10.1 g) in benzene (20 ml) was added hydrazine monohydrate (1.85 g). The mixture was refluxed with heating for 2 hours. After the reaction liquid was concentrated under a vacuum, the deposited crystal was recrystallized from a chloroform/n-hexane mixed solution, thereby yielding 9.61 g (97%) of 4-methoxybenzaldehyde azine.

To a solution of 4-methoxybenzaldehyde azine (1.03 g) in tetrahydrofuran anhydride (20 ml) was added sodium cyanoborohydride (0.60 g). Then, 10% methanol solution of hydrogen chloride was added thereto until pH becomes about 3. Then, the resulting mixture was stirred at room temperature for 1 hour. A potassium carbonate aqueous solution was added to the reaction solution so as to make basic, then extracted with ethyl acetate. After the extract was concentrated under a vacuum, 10% hydrogen chloride methanol solution was added to the residue to form a hydrochloride. Then, upon recrystallization from a methanol/diethylether, 1.00 g (75%) of 1,2- bis(4-methoxyphenylmethyl) hydrazine dihydrochloride was obtained.

To a mixed solution of toluene (8 ml) and methanol (12 ml) were added 1,2-bis(4- methoxyphenylmethyl)hydrazine dihydrochloride (0.99 g) and 1,3- dimorpholino-2-nitropropane (0.75 g). The mixture was refluxed with heating for 3 hours. The reaction solution was concentrated under a vacuum, purified by silica gel column chromatography (n-hexane:ethyl acetate=3:1), thereby yielding 0.88 g (86%) of 1,2-bis (4-methoxyphenylmethyl)-4-nitropyrazolidine.

To a solution of 1,2-bis(4-methoxyphenylmethyl)-4-nitropyrazolidine (0.88 g) in diethylether anhydride (20 ml) was gradually added lithium aluminum hydride (0.38 g) while being cooled with ice. After being refluxed with heating for two hours, the reaction liquid, with an aqueous sodium potassium tartrate solution added thereto, was extracted with ether. The extract was concentrated under a vacuum, thereby yielding 0.80 g of a raw product of the aimed compound.

In the following, examples of the compound in accordance with the present invention will be explained.

Example 1

Synthesis of N-(1,2-diethyl-4-pyrazolidinyl)-3,4-digeranyloxybenzamide

In a manner similar to Reference Example 1, ethyl 3,4-(dihydroxybenzoate (9.10 g) was reacted with geranyl bromide (21.7 g) and then hydrolyzed to yield 13.1 g (62%) of 3,4- digeranyloxybenzoic acid.

In a manner similar to Example 5, from 3,4- digeranyloxybenzoic acid (1.50 g) and 4-amino-1,2-diethylpyrazolidine (0.51 g), 1.28 g (62%) of the aimed compound was obtained.
mp 61.8°–63.0° C.
$^1$H-NMR (CDCl$_3$): δ 1.11(6H, t, J=7.3Hz), 1.59(6H, s), 1.66(6H, s), 1.73(3H, s), 1.74(3H, s), 2.06–2.12(8H, m), 2.66–2.74(4H, m), 2.81(2H, dd, J=4.4, 11.2 Hz), 3.29(2H, dd, J=6.8, 11.2 Hz,), 4.66(4H, d, J=6.4 Hz), 4.77–4.84(1H, m), 5.06–5.08(2H, m), 5.47–5.53(2H, m), 6.26(1H, d, J=7.3 Hz), 6.85(1H, d, J=8.3 Hz), 7.23(1H, dd, J=2.0, 8.3 Hz), 7.40(1H, d, J=2.0 Hz).

Example 2

Synthesis of N-(1,2-diethyl-4-pyrazolidinyl)-2,4-digeranyloxybenzamide

To a solution of 2,4- dihydroxybenzoic acid (1.00 g) in tetrahydrofuran anhydride (20 ml) were added 1-hydroxybenzotriazole (1.05 g) and N,N'-dicyclohexyl carbodiimide (1.34 g) while being cooled with ice. After the resulting mixture was stirred for 30 minutes, 4-amino-1,2-diethylpyrazolidine (0.93 g) was added thereto and the mixture was stirred for one night at room temperature. The reaction solution, with chloroform added thereto, was washed with brine and then dried over sodium sulfate anhydride. The resulting organic layer was concentrated under a vacuum and thus formed residue was purified by silica gel column chromatography (chloroform: methanol= 20:1) so as to yield 1.17 g (65%) of N-(1,2-diethyl-4-pyrazolidinyl)-2,4- dihydroxybenzamide.

To a solution of this compound (1.17 g) in acetone (30 ml) were added potassium carbonate (2.32 g) and geranyl bromide (2.73 g). After being refluxed with heating for one night, the reaction liquid was filtered and the filtrate was concentrated under a vacuum. The residue was dissolved in chloroform, washed with brine successively, dried over sodium sulfate anhydride, and then concentrated under a vacuum. The residue was purified by silica gel column chromatography (hexane:ethyl acetate=2:1), thereby yielding 0.53 g (23%) of the aimed compound.
$^1$H-NMR (CDCl$_3$): δ 1.09(6H, t, J=7.3 Hz), 1.61(6H, s), 1.68(6H, s), 1.75(6H, s), 2.09–2.13(8H, m), 2.62–2.77(6H, m), 3.34(2H, dd, J=7.3, 11.2Hz), 4.59(4H, dd, J=6.3, 11.2 Hz), 4.79–4.84(1H, m), 5.07–5.09(2H, m), 5.48–5.56(2H, m), 6.51(1H, d, J=2.0 Hz), 6.59(1H, dd, J=2.4, 8.8 Hz), 8.15(1H, d, J=8.8 Hz), 8.22(1H, d, J=6.8 Hz).

Example 3

Synthesis of N-(1,2-diethyl-4-pyrazolidinyl)-2,5-digeranyloxybenzamide In a manner similar to Reference Example 1, from ethyl 2,5-dihydroxy benzoate (9.10 g) and geranyl bromide (21.7 g), 16.4 g (76%) of 2,5-digeranyloxy benzoic acid was obtained.

In a manner similar to Example 5, from 2,5- digeranyloxybenzoic acid (1.57 g) and 4-amino-1,2-diethylpyrazolidine (0.53 g), 1.20 g (62%) of the aimed compound was obtained
$^1$H-NMR (CDCl$_3$): δ 1.09(6H, t, J=7.3 Hz), 1.60(3H, s), 1.61(3H, s), 1.67(3H, s), 1.68(3H, s), 1.73(3H, s), 1.74(3H, s), 2.07–2.13(8H, m), 2.66(4H, q, J=7.3 Hz), 2.76(2H, m), 3.35(2H, dd, J=7.3, 11.2 Hz), 4.54(2H, d, J=7.3 Hz), 4.60 (2H, d, J=7.3Hz), 4.80–4.85(1H, m), 5.07–5.09(2H, m), 5.46–5.54(2H, m), 6.90(1H, d, J=9.3 Hz), 6.98–7.01(1H, m), 7.78(1H, d, J=2.4 Hz), 8.48(1H, d, J=7.3 Hz).

Example 4

Synthesis of N-(1,2-diethyl-4- pyrazolidinyl)3,5-digeranyloxybenzamide

In a manner similar to Reference Example 1, from methyl 3,5-dihydroxy benzoate (8.40 g) and geranyl bromide (21.7 g), 10.1 g (47%) of 3,5-digeranyloxy benzoic acid was obtained.

In a manner similar to Example 5, from 3,5- digeranyloxybenzoic acid (0.65 g) and 4-amino-1,2-diethylpyrazolidine (0.22 g), 0.67 g (80%) of the aimed compound was obtained.
$^1$H-NMR (CDCl$_3$): δ 1.10(6H, t, J=7.3 Hz), 1.61(6H, s), 1.68(6H, s), 1.74(6H, s), 2.07–2.14(8H, m), 2.68(4H, dd, J=2.0, 7.3 Hz), 2.78(2H, dd, J=4.4, 11.2 Hz), 3.28(2H, dd, J=6.8, 11.2 Hz), 4.54(4H, d, J=6.4 Hz), 4.67–4.83(1H, m), 5.10–5.11(2H, m), 5.48(2H, dd, J=5.4, 6.8 Hz), 6.28(1H, d, 37.3 Hz), 6.61(1H, d, J=2.0 Hz), 6.88(2H, d, J=2.0 Hz).

Example 5–7

Synthesis of N-(1,2-diethyl-4-pyrazolidinyl)-2-geranyloxybenzamide

In a manner similar to Reference Example 1, methyl 2-hydroxybenzoate (7.61 g) was reacted with geranyl bromide (10.9 g) and then hydrolyzed to yield 10.2 g (75%) of 2- geranyloxybenzoic acid.

2-geranyloxybenzoic acid (1.36 g) was dissolved in dichloromethan (20 ml) and 1-hydroxybenzotriazole (0.80 g) and 1-(3-dimethylaminopropyl)-3-ethyl carbodiimide hydrochloride (1.14 g) were added thereto while being cooled with ice. After the resulting mixture was stirred for 30 minutes, 4-amino-1,2-diethyl pyrazolidine (0.71 g) was added thereto and the mixture was stirred for one night at room temperature. The reaction liquid was washed with brine and then dried over sodium sulfite anhydride. Thereafter, the solvent was evaporated under a vacuum. The residue was purified by silica gel column-m chromatography (chloroform:methanol=30:1), thereby yielding 1.71 g (87%) of the aimed compound.

$^1$H-NMR (CDCl$_3$): δ 1.09(6H, t, J=7.3 Hz), 1.61(3H, s), 1.69(3H, s), 1.76(3H, s), 2.09–2.17(4H, m), 2.64–2.69(4H, m), 2.74–2.78(2H, m), 3.35(2H, d(, J=7.3, 12.2 Hz), 4.66 (2H, d, J=6.8 Hz), 4.79–4.88(1H, m), 5.06–5.10(1H, m), 5.53–5.56(1H, m), 6.97(1H, d, J=7.8 Hz), 7.05–7.09(1H, m), 7.40–7.45(1H, m), 8.21(1H, dd, J=2.0, 7.8 Hz), 8.36(1H, d, J=6.8 Hz).

Example 6
Synthesis of N-(1,2-diethyl-4- pyrazolidinyl)-3- geranyloxybenzamide

In a manner similar to Reference Example 1, from methyl 3-hydroxybenzoate (7.61 g) and geranyl bromide (10.9 g), 10.2 g (75%) of 3-geranyloxybenzoic acid was obtained.

In a manner similar to Example 5, from 3-geranyloxybenzoic acid (1.78 g) and 4-amino-1,2-diethylpyrazolidine (1.05 g), 1.44 g (56%) of the aimed compound was obtained.

$^1$H-NMR (CDCl$_3$): δ 1.10(6H, t, J=7.3 Hz), 1.61(3H, s), 1.68(3H, s), 1.75(3H, s), 2.07–2.14(4H, m), 2.67–2.72(4H, m), 2.82(2H, m), 3.29(2H, dd, J=6.8, 11.2 Hz), 4.68(2H, d, J=6.3 Hz), 4.78–4.85(1H, m), 5.08–5.11(1H, m), 5.47–5.50 (1H, m), 6.35(1H, d, J=7.3 Hz), 7.03–7.06(1H, m), 7.23–7.37(3H, m).

Example 7
Synthesis of N-(1,2-diethyl-4-pyrazolidinyl)-4- geranyloxybenzamide

To a solution of 4- geranyloxybenzoic acid (1.10 g) in chloroform (20 ml), triethylamine (1.11 ml) and a solution of diphenylphosphinic chloride (0.95 g) in chloroform (5 ml) were successively added. After the reaction solution was stirred for 30 minutes, 4-amino-1,2-diethylpyrazolidine (0.57 g) was added and then the mixture was stirred at room temperature for one night. The reaction solution was washed with aqueous solution of sodium hydrogencarbonate, dried over sodium sulfate anhydride, and then concentrated under a vacuum. The residue was purified by silica gel column chromatography (chloroform:methanol=20:1) and then recrystallized from n-hexane, thereby yielding 1.39 g (87%) of the aimed compound.
mp 95.5°–97.0° C.

$^1$H-NMR (CDCl$_3$): δ 1.10(6H, t, J=7.3 Hz), 1.60(3H, s), 1.68(3H, s) 1.74(3H, s), 2.04–2.20(4H, m), 2.64–2.78(4H, m), 2.82(2H, dd, J=4.1, 11.2 Hz), 3.28(2H, dd, J=6.8, 11.2 Hz), 4.58(2H, d, J=6.4 Hz), 4.75–4.88(1H, m), 5.09(1H, m), 5.47(1H, m), 6.37(1H, d, J=6.4 Hz), 6.92(2H, d, J=8.3 Hz), 7.72(2H, d, J=8.3 Hz).

N-(1,2-diethyl-4-pyrazolidinyl)-4-geranyloxybenzamide (625 mg) was dissolved in ethyl acetate (5 ml) and phosphoric acid (0.11 ml) was added thereto. After the resulting mixture was stirred for 5 minutes, the reaction solution was washed with water, and the solvent was evaporated. The residue was dried under a vacuum to yield 685 mg of a phosphate of the aimed compound.

$^1$H-NMR (CDCl$_3$): δ 1.10–1.70(6H, brs), 1.61(3H, s), 1.68 (3H, s), 1.74(3H, s), 2.04–2.20(4H, m), 2.90–4.20(8H, brs), 4.57(2H, d, J=6.3 Hz), 5.09(1H, t, J=6.3Hz), 5.29(1H, brs), 5.45–5.50(1H, m), 6.94(2H, d, J=8.5 Hz), 8.02(2H, d, J=8.5 Hz), 8.82(1H, m), 13.00–13.70(1H, brs).

N-(1,2-diethyl-4-pyrazolidinyl)-4-geranyloxybenzamide (502 mg) was dissolved in methanol (5 ml) and DL-tartaric acid (192 mg) was added thereto. After being stirred for 5 minutes, the reaction liquid was concentrated under a vacuum. The residue was dried under a vacuum to yield 690 mg of a tartrate of the aimed compound.

$^1$H-NMR (CDCl$_3$): δ 1.24(6H, t, J=6.8 Hz), 1.60(3H, s), 1.67(3H, s), 1.72(3H, s), 2.04–2.12(4H, m), 3.08–3.13(2H, m), 3.20–3.24(2H, m), 3.44–3.57(4H, m), 4.41(2H, s), 4.53 (2H, d, J=6.4Hz), 5.07–5.16(2H, m), 5.44–5.47(1H, m), 6.91(2H, d, J=8.8 Hz,), 7.92(2H, d, J=8.8 Hz), 8.86(1H, brs).

Example 8
Synthesis of N-(1,2-diethyl-4-pyrazolidinyl)-4- neryloxybenzamide

To a solution of N-chlorosuccinimide (10.0 g) and dimethylsulfide (6.56 ml) in dichloromethane (200 ml) was added nerol (7.71 g) while being cooled with ice. The mixture was stirred at 0° C. for 4 hours. The reaction solution was washed with brine and dried over sodium sulfate anhydride. Then, the solvent was evaporated, thereby yielding a raw product of neryl chloride. In a manner similar to Reference Example 1, this raw product was reacted with methyl 4- hydroxybenzoate (7.61 g) and then hydrolyzed to yield 7.47 g (55%) of 4- neryloxybenzoic acid.

In a manner similar to Example 5, from neryloxybenzoic acid (0.87 g) and 4-amino-1,2-diethylpyrazolidine (0.46 g), 0.89 g (70%) of the aimed compound was obtained.
mp 69.0°–69.8° C.

$^1$-NMR (CDCl$_3$): δ 1.11(6H, t, J=7.3 Hz), 1.60(3H, s), 1.6(3H, s), 1.81(3H, s), 2.11–2.17(4H, m), 2.66–2.73(4H, m) 2.74–2.82(2H, m), 3.29(2H, dd, J=7.3, 11.2 Hz), 4.54(2H, d, J=6.4 Hz), 4.80–4.82(1H, m), 5.11–5.12(1H, m), 5.48–5.51 (1H, m), 6.23(1H, d, J=7.3 Hz), 6.92(2H, d, J=6.8 Hz), 7.71(2H, d, J=6.8 Hz).

Example 9
Synthesis of N-(1,2-diethyl-4-pyrazolidinyl)-4-(trans, trans-farnesyloxy) benzamide In a manner similar to Reference Example 1, from methyl 4-hydroxybenzoate (5.33 g) and trans, trans-farnesyl bromide (10.0 g, 7.58 g (63%) of 4-(trans, trans-farnesyloxy) benzoic acid was obtained.

In a manner similar to Example 5, from 4-(trans, trans-farnesyloxy)benzoic acid (1.50 g) and 4-amino-1,2-diethylpyrazolidine (0.63 g), 2.05 g (100%) of the aimed compound was obtained.
mp 63.5°–65.2° C.

$^1$H-NMR (CDCl$_3$): δ 1.10(6H, t, J=7.3 Hz), 1.60(6H, s), 1.68(2H, s), 1.75(3H, s), 1.95–2.15(8H, m), 2.66–2.73(4H, m), 2.81(2H, dd, J=4.4, 11.2 Hz), 3.29(2H, dd, J=6.8, 11.2 Hz), 4.57(2H, d, J=6.8 Hz), 4.79–4.85(1H, m), 5.07–5.12 (2H, n), 5.46–5.49(1H, m), 6.25(1H, d, J=7.3 Hz), 6.93(2H, d, J=6.8 Hz), 7.71(2H, d, J=6.8 Hz).

Example 10
Synthesis of N-(1,2-diethyl-4-pyrazolidinyl)-4-(3-methyl-2- butenyloxy) benzamide In a manner similar to Reference Example 1, from methyl 4-hydroxybenzoate (7.61 g) and 1-bromo-3-methyl-2-butene (7.45 g), 5.86 g (57%) of 4-(3-methyl 2-butenyloxy) benzoic acid was obtained.

In a manner similar to Example 5, from 4-(3-methyl-2-butenyloxy) benzoic acid (1.50 g) and 4-amino1,2-diethylpyrazolidine (1.65 g), 1.17 g (49%) of the aimed compound was obtained.
mp 96.4°–98.0° C.

$^1$H-NMR (CDCl$_3$): δ 1.11(6H, t, J=7.3 Hz), 1.75(3H; s), 1.80(3H, s), 2.66–2.74(4H, m), 2.82(2H, dd, J=4.4, 11.2 Hz), 3.29(2H, dd, J=6.8, 11.2 Hz), 4.55(2H, d, J=6.8 Hz), 4.79–4.84(1H, m), 5.48(1H, t, J=1.5 Hz), 6.26(1H, d, J=7.3 Hz), 6.93(2H, d, J=6.8 Hz), 7.72(2H, d, J=6.8 Hz).

Synthesis of 4-geranyloxy-N-[1,2-bis(4-methoxyphenylmethyl)-4-pyrazolidinyl]benzamide To a solution of 4-geranyloxybenzoic acid (19.2 g) in tetrahydrofuran anhydride (200 ml) was added 1,1'-carbonyldiimidazole (11.4 g). After being stirred for 2 hours at room temperature, the reaction solution, with water added thereto, was extracted with ethyl acetate. The extract was dried over sodium sulfate anhyride and then the solvent was evaporated under a vacuum. The residue was recrystallized from n-hexane, thereby yielding 16.7 g (79%) of 4-geranyloxybenzoylimidazole.

To a solution of 4-amino-1,2-bis(4-methoxyphenylmethyl)pyrazolidine (0.80 g) in tetrahydrofuran anhydride (20 ml) was added 4-geranyloxybenzoylimidazole (0.79 g). The mixture was stirred at room temperature for one night. The reaction solution, with water added thereto, was extracted with ethyl acetate. The extract was concentrated under a vacuum and the residue was purified by silica gel column chromatography (chloroform) and then recrystallized from ethyl acetate, thereby yielding 0.65 g (45%) of the aimed compound.
mp 122.9°–123.7° C.
$^1$H-NMR (CDCl$_3$): δ 1.61(3H, s), 1.68(3H, s), 1.74(3H, s), 2.05–2.19(4H, m), 2.79(2H, dd, J=4.4, 11.2 Hz), 326(2H, dd, J=6.8, 11.2 Hz), 3.73(2H, d, J=12.5 Hz), 3.78(6H, s), 3.85(2H, d, J=12.5 Hz), 4.58(2H, d, J=6.4 Hz), 4.72–4.83 (1H, n), 5.09(1H, t, J=6.4 Hz), 5.47(1H, dd, J=5.6, 6.6 Hz), 6.01(1H, d, J=7.8Hz), 6.83(4H, d, J=8.5 Hz), 6.91(2H, d, J=8.8 Hz), 7.23(4H, d, J=8.5 Hz), 7.61(2H, d, J=8.8 Hz).

Example 12
Synthesis of N-(1,2-diethyl-4-pyrazolidinyl)-4-geranyloxycinnamamide

To a solution of 4-hydroxycinnamic acid (16.4 g) in ethanol (100 ml) was added sulfuric acid (10 ml). The mixture was refluxed with heating for 4 hours, Aqueous sodium bicarbonate solution was added to the reaction solution so as to make basic. Then, the reaction solution was extracted with chloroform. The extract was dried over sodium sulfate anhydride and then concentrated under a vacuum to yield a raw product of ethyl 4-hydroxycinnamate. In a manner similar to Reference Example 1, this raw product was reacted with geranyl bromide (21.7 g) and then hydrolyzed to yield 13.9 g (46%) of 4-geranyloxycinnamic acid.

In a manner similar to Example 5, from ethyl 4-geranyloxycinnamate (1.23 g) and 4-amino-1,2-diethylpyrazoidine (0.59 g), 1.57 g (90%) of the aimed compound was obtained.
mp 64.0°–65.5° C.
$^1$H-NMR (CDCl$_3$): δ 1.10(6H, t, J=7.3 Hz), 1.60(3H, s), 1.67(3H, s), 1.74(3H, s), 2.07–2.14(4H, m), 2.65–2.79(6H, m), 3.24–3.29(2H, m), 4.55(2H, d, J=7.3 Hz), 4.73–4.79(1H, m), 5.07–5.10(1H, m), 5.46–5.49(1H, m), 5.76(1H, d, J=6.8 Hz), 6.22(1H, d, J=5.1 Hz), 6.89(2H, d, J=8.8 Hz), 7.43(2H, d, J=8.8 Hz), 7.58(1H, d, J=5.1 Hz).

Example 13
Synthesis of N-(1,2-diethyl-4-pyrazolidinyl)-4-geranyloxyphenylacetamide To a solution of 4-hydroxyphenylacetic acid (3.00 g) in ethanol (50 ml) was added sulfuric acid (5 ml). The mixture was refluxed with heating for 4 hours. Aqueous sodium bicarbonate solution was added to the reaction solution so as to make basic. Then, the reaction solution was extracted with chloroform. The extract was dried over sodium sulfate anhydride and then concentrated under a vacuum to yield a raw product of ethyl 4-hydroxyphenylacetate. In a manner similar to Reference Example 1, this raw product was reacted with geranyl bromide (7.10 g) and then hydrolyzed to yield 3.54 g (61%) of 4-geranylophenylacetic acid.

To a solution of 4-geranyloxyphenylacetic acid (1.50 g) in tetrahydrofuran anhydride (30 ml) were added 1-hydroxybenzotriazole (0.85 g), N,N'-dicyclohexyl carbodiimide (1.29 g), and 4-amino-1,2-diethylpyrazolidine (0.75 g) while being cooled with ice and then the mixture was stirred for 6 hours at room temperature. The reaction solution was filtered so as to filter out the deposited product and the filtrate was concentrated under a vacuum. The residue was purified by silica gel column chromatography (chloroform:methanol=20:1), thereby yielding 2.05 g (95%) of the aimed compound.
$^1$-NMR (CDCl$_3$): δ 1.02(6H, t, J=7.3 Hz), 1.61(3H, s), 1.68(3H, s), 1.74(3H, s), 2.07–2.14(4H, m), 2.52–2.59(6H, m), 3.12–3.17(2H, m), 3.48(2H, s), 4.53(2H, d, J=6.8 Hz), 4.57–4.61(1H, m), 5.08–5.11(1H, m), 5.47–5.50(1H, m), 5.56–5.58(1H, m), 6.89(2H, d, J=8.8 Hz), 7.13(2H, d, J=8.8 Hz).

Example 14
Synthesis of 1,2-diethyl-4-(4-geranyloxyphenylmethoxy) pyrazolidine

To a suspension of N-chorosuccinimide (1.15 g) in dichloromethane (40 ml) was added dimethylsulfide (0.72 g) while being cooled with ice. Then, a solution of 4-geranyloxybenzyl alcohol (1.50 g) in dichloromethane (10 ml) was added thereto and the resulting mixture was stirred for 3 hours at room temperature. The reaction solution, with brine added thereto, was extracted with ethyl acetate. The extract was concentrated under a vacuum to yield a raw product of 4-geranyloxybenzyl chloride.

Sodium hydride (0.35 g) was suspended in hexane. After the supernatant was removed, N,N-dimethylformamide (10 ml) was added to the remaining suspension. Then, 1,2-diethyl-4-hydroxypyrazolidine (0.84 g) and a solution of the above-yielded raw product of 4-geranyloxybenzyl chloride in N,N-dimethylformamide (10 ml) were added thereto. After being stirred at room temperature for one night, the reaction solution, with ice water added thereto, was extracted with ethyl acetate. The extract was washed with brine, dried over sodium sulfate anhydride, and then concentrated under a vacuum The residue was purified by silica gel column chromatography (chloroform:methanol=40:1), thereby yielding 0.82 g (37%) of the aimed compound.
$^1$NMR (CDCl$_3$): δ 1.08(6H, t, J=7.3 Hz), 1.60(3H, s), 1.68(3H, s), 1.73(3H, s), 2.04–2.15(4H, m), 2.65(4H, q, J=7.3 Hz), 3.01(4H, d, J=4.8 Hz), 4.28–4.33(1H, m), 4.42 (2H, s), 4.51(2H, d, J=6.4 Hz), 5.07–5.11(1H, m), 5.47–5.50 (1H, m), 6.88(2H, d, J=8.8 Hz), 7.23(2H, d, J=8.8 Hz).

Example 15
Synthesis of N-(1,2-diethyl-4-pyrazolidinyl)-(4-geranyloxyphenylmethyl)amine To a suspension of lithium aluminum hydride (0.27 g) in tetrahydrofuran anhydride (40 ml) was added a solution of N-(1,2-diethyl-4-pyrazolidinyl)-4-geranyloxybenzamide (0.89 g) in tetrahydrofuran anhydride (10 ml) dropwise while being cooled with ice. After being refluxed with heating for 5 hours, the reaction solution, with aqueous solution sodium potassium tartrate added thereto, was extracted with dichloromethane. The extract was concentrated under a vacuum and thus obtained residue was purified by silica gel column chromatography (chloroform:methanol=40:1), thereby yielding 0.31 g (36%) of the aimed compound.
$^1$H-NMR (CDCl$_3$): δ 1.07(6H, t, J=7.3 Hz), 1.60(3H, s), 1.68(3H, s), 1.73(3H, s), 2.08–2.13(4H, m), 2.63–2.68(6H, m), 3.12–3.17(2H, m), 3.54–3.59(1H, m), 3.71(2H, s), 4.52 (2H, d, J=6.4 Hz), 5.07–5.09(1H, m), 5.47–5.50(1H, m), 6.86(2H, d, J=8.8 Hz), 7.21(2H, (1H, J=8.8 Hz).

Example 16
Synthesis of 1,2-diethyl-4-pyrazolidinyl 4-geranyloxybenzoate

To a solution of 4-geranyloxybenzoic acid (1.50 g) in dichloromethane (20 ml) was added 1,2-diethyl-4-hydroxypryrazolidine (0.87 g) dropwise while being cooled with ice. N,N'-dicyclohexylcarbodiimide (1.35 g) and 4-dimethylaminopyridine (0.53 g) were added to this reaction solution, and the resulting mixture was stirred for 8 hours at room temperature. The reaction solution was filtered so as to filter out the deposited product. The filtrate was washed with brine, dried over sodium sulfate anhydride, and then concentrated under a vacuum. The residue was purified by silica gel column chromatography (chloroform:methanol=50:1), thereby yielding 0.97 g (44%) of the aimed compound.

$^1$H-NMR (CDCl$_3$): δ 1.12(6H, t, J=7.3 Hz), 1.60(3H, s), 1.67(3H, s), 1.77(3H, s), 2.07–2.14(4H, m), 2.70(4H, q, J=7.3 Hz), 3.14–3.18(2H, m), 3.24–3.28(2H, m), 4.59(2H, d, J=6.3 Hz), 5.07–5.10(1H, m), 5.45–5.49(1H, m), 5.58–5.61 (1H, m), 6.92(2H, d, J=8.8 Hz), 7.96(2H, d, J=8.8 Hz).

Example 17
Synthesis of N-(1,2-diethyl-4-pyrazolidinyl)-4-geranyloxythiobenzamide To a solution of N-(1,2-diethyl-4-pyrazolidinyl)-4-geranyloxybenzamide (1.50 g) in toluene (50 ml) was added Lawesson's reagent (0.76 g). After the reaction solution was refluxed with heating for 30 minutes, ethyl acetate was added thereto. Then, the reaction solution was washed with aqueous sodium bicarbonate solution and then with brine. Its organic layer was concentrated under a vacuum and thus obtained residue was pulled by silica gel column chromatography (chloroform:methanol=30:1), thereby yielding 1.09 g (70%) of the aimed compound.

$^1$H-NMR (CDCl$_3$): δ 1.11(6H, t, J=7.3 Hz), 1.61(3H, s), 1.68(3H, s), 1.74(3H, s), 2.07–2.14(4H, m), 2.70(4H, q, J=7.3 Hz), 2.97–3.01(2H, m), 3.32–3.37(2H, m), 4.58(2H, d, J=6.3 Hz), 5.07–5.09(1H, m), 5.24–5.27(1H, m), 5.45–5.48 (1H, m), 6.89(2H, d, J=8.8 Hz), 7.68–7.73(1H, m), 7.75(2H, d, J=8.8 Hz).

What is claimed is:

1. A pyrazolidine derivative or a salt thereof expressed by the following formula 1:

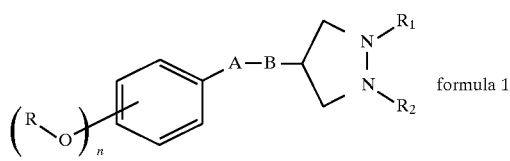

formula 1 wherein A represents a group expressed by —CH$_2$—, —CO—, —CS—, —CH$_2$CO—, or —CH=CH—CO—; B represents a group expressed by —O— or —NH—; n is an integer of 1 or 2; R represents an alkenyl group; and R$_1$, and R$_2$ represent a lower alkyl or benzyl group.

2. A pyrazolidine derivative or a salt thereof according to claim 1, wherein R is a branched alkenyl group.

3. A pyrazolidine derivative or a salt thereof according to claim 2, wherein R is a group expressed by R$_3$—C(CH$_3$)=CH—CH—$_2$— in which R$_3$ represents methyl, prenyl, or geranyl group.

4. A pyrazolidine derivative or a salt thereof according to claim 1, wherein each of R$_1$ and R$_2$ is ethyl group.

5. A pyrazolidine derivative or a salt thereof according to claim 1, wherein A is —CO— group and B is —NH— group.

6. A pyrazoldine derivative or a salt thereof according to claim 1, expressed by the following formula 2:

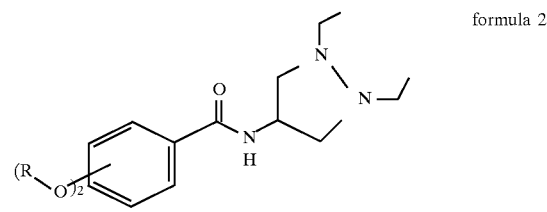

formula 2 wherein wherein R is a group expressed by R$_3$—C(CH$_3$)=CH—CH$_2$— in which R$_3$ represents an alkenyl group.

7. A pyrazolidine derivative or a salt thereof according to claim 6, wherein R$_3$ is prenyl group.

8. A pyrazolidine derivative or a salt thereof according to claim 1, expressed by the following formula 3:

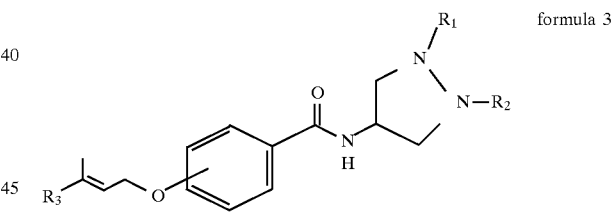

formula 3 wherein R$_3$ represents methyl, prenyl, or geranyl group and R$_1$ and R$_2$ represent a lower alkyl or benzyl group.

9. A pyrazolidine derivative or a salt thereof according to claim 8, wherein each of R$_1$ and R$_2$ is ethyl group.

10. A pyrazolidine derivative or a salt thereof according to claim 8 or wherein R$_3$ is prenyl group.

11. A pyrazolidine derivative or a salt thereof according to claim 1, expressed by the following formula 4:

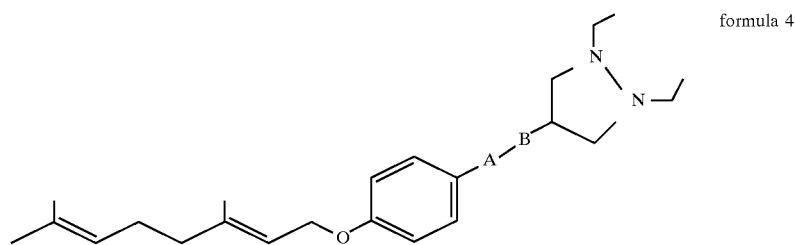

formula 4 wherein A represents a group expressed by —CH$_2$—, —CO—, —CS—, —CH$_2$CO—, or —CH=CH—CO— and B represents a group expressed by —O— or —NH—.

12. A radical scavenger comprising, as an effective ingredient, a pyrazolidine derivative or a pharmacologically acceptable salt thereof according to claim 1, together with a pharmaceutically acceptable carrier and/or adjuvant.

13. A brain infarction depressant comprising, as an effective ingredient, a pyrazolidine derivative or a pharmacologically acceptable salt thereof according to claim 1, together with a pharmaceutically acceptable carrier and/or adjuvant.

14. A brain edema depressant comprising, as an effective ingredient, a pyrazolidine derivative or a pharmacologically acceptable salt thereof according to claim 1, together with a pharmaceutically acceptable carrier and/or adjuvant.

15. A method for inhibiting a brain infarction in man or mammals, which compises administration to it of an effective amount of a pyrazolidine derivative or a pharmacologically acceptable salt thereof according to claim 1.

16. A method for inhibiting a brain edema in man or mammals, which compises administration to it of an effective amount of a pyrazolidine derivative or a pharmacologically acceptable salt thereof according to claim 1.

17. A pyrazolidine derivative or a salt thereof according to claim 1, wherein R is neryl group.

* * * * *